United States Patent [19]
Coffman

[11] Patent Number: 5,981,736
[45] Date of Patent: Nov. 9, 1999

[54] ONE STEP DEVICE AND PROCESS FOR CONCENTRATION AND PURIFICATION OF BIOLOGICAL MOLECULES

[75] Inventor: Jonathan L. Coffman, Princeton, Mass.

[73] Assignee: Life Technologies, Inc., Rockville, Md.

[21] Appl. No.: 09/104,795

[22] Filed: Jun. 25, 1998

Related U.S. Application Data

[60] Provisional application No. 60/051,756, Jun. 27, 1997.

[51] Int. Cl.[6] .................................................. C07H 21/04
[52] U.S. Cl. ................. 536/25.4; 536/25.41; 536/25.42; 210/635; 210/656
[58] Field of Search ............................... 536/25.4, 25.41, 536/25.42; 210/635, 656

[56] References Cited

U.S. PATENT DOCUMENTS

| | | | |
|---|---|---|---|
| 3,433,782 | 3/1969 | Kreiser | 536/25.4 |
| 3,821,193 | 6/1974 | Fare et al. | 536/25.4 |
| 4,515,889 | 5/1985 | Klose et al. | 435/4 |
| 4,623,723 | 11/1986 | Keller et al. | 536/25.4 |
| 4,699,717 | 10/1987 | Riesner et al. | 210/635 |
| 4,719,011 | 1/1988 | Shalon et al. | 210/198.2 |
| 4,810,381 | 3/1989 | Hagan et al. | 210/502.1 |
| 4,830,969 | 5/1989 | Holmes | 435/259 |
| 4,921,952 | 5/1990 | Longmire et al. | 536/25.4 |
| 4,923,978 | 5/1990 | McCormick | 536/25.4 |
| 4,935,142 | 6/1990 | Sternberg | 210/634 |
| 4,935,342 | 6/1990 | Seligson et al. | 435/6 |
| 4,997,932 | 3/1991 | Reardon et al. | 536/25.4 |
| 5,057,426 | 10/1991 | Henco et al. | 435/270 |
| 5,075,430 | 12/1991 | Little | 536/25.4 |
| 5,300,635 | 4/1994 | Macfarlane | 536/25.4 |
| 5,316,680 | 5/1994 | Frechet et al. | 210/635 |
| 5,342,931 | 8/1994 | Woodard et al. | 536/25.4 |
| 5,561,064 | 10/1996 | Marquet et al. | 435/320.1 |
| 5,637,687 | 6/1997 | Wiggins | 536/25.4 |
| 5,728,822 | 3/1998 | Macfarlane | 536/25.41 |
| 5,772,888 | 6/1998 | Liu et al. | 210/634 |

FOREIGN PATENT DOCUMENTS

| | | |
|---|---|---|
| 0268946 | 6/1988 | European Pat. Off. . |
| 0270017 | 6/1988 | European Pat. Off. . |
| 0376080 | 4/1990 | European Pat. Off. . |
| 0389063 | 9/1990 | European Pat. Off. . |
| 0012900 | 2/1978 | Japan . |
| 0638599 | 12/1978 | U.S.S.R. . |
| 9105606 | 5/1991 | WIPO . |
| 9107422 | 5/1991 | WIPO . |
| 9311221 | 6/1993 | WIPO . |

*Primary Examiner*—Eric Crane
*Attorney, Agent, or Firm*—Foley & Lardner

[57] ABSTRACT

A device for one step purification of a desired biological molecule from a sample, wherein the device comprises a housing loaded with an adsorptive media of a known volume on top of a size exclusion media of a known volume, and a method of purifying biological molecules using the same.

24 Claims, 1 Drawing Sheet

ONE STEP DEVICE AND PROCESS FOR CONCENTRATION AND PURIFICATION OF BIOLOGICAL MOLECULES

This application claims provisional Application No. 60/051,765 filed Jun. 27, 1997.

FIELD OF INVENTION

The present invention relates to devices and methods for concentrating and purifying biological molecules.

BACKGROUND OF INVENTION

There are many devices used in purification of molecules where an adsorptive media is packed into the bottom of a syringe-like object, or in the wells of a multiwell plate. Typically, the target solute is eluted in a buffer that is unfavorable to further analysis, and the solute must be further processed to remove or exchange the eluting buffer with another buffer favorable for further analysis or other use.

An example of such is an elution from an ion exchange column, wherein the solute of interest is eluted from the column in a high salt buffer. However, many subsequent analyses of the solute of interest, including, e.g., electrophoresis or enzymatic digests of plasmid DNA, cannot be performed satisfactorily in this high salt environment. Thus, at present, such a sample is often desalted with dialysis or with a separate gel permeation or size exclusion chromatography ("SEC") device, or for plasmid purification, the DNA is precipitated from the salt solution with a variety of precipitants, including ethanol, isopropanol, PEG4000, and the like. (See, e.g., U.S. Pat. No. 5,057,426 to Henco et al., which is incorporated herein by reference.)

In addition, prior to the present invention, adsorptive chromatography devices which used multiwell plates required a two step/two plate method in order to achieve purification, by e.g., ion exchange, and subsequent separation of the desired product from the high salt content of the elution buffer. This required using two separate chromatography steps and two multiwell plates, thereby undesirably increasing both the time and cost of such purification methods.

SUMMARY OF INVENTION

The device and methods of the present invention overcome the disadvantages of previous means of purifying biological molecules by combining the adsorptive chromatography step with the SEC step (e.g., desalting), thereby allowing the desired product or biological molecules of interest to be eluted in a buffer that facilitates further processing, such as gene transfection or analysis by electrophoresis, using a single chromatography process and a single plate.

In one aspect the present invention relates to a device for purifying or separating a desired product or biological molecule of interest which comprises a housing having an outlet disposed at a bottom end, wherein a porous material is disposed over the outlet, a size exclusion media portion comprising a volume of a size exclusion media packed in the housing on top of said porous material, and an adsorptive media portion comprising a volume of adsorptive media packed in the housing on top of said size exclusion media portion. In a preferred embodiment, the housing is a well of a multiwell plate.

In another embodiment, the device further comprises a removable porous material, such as a porous frit or membrane, disposed on top of the adsorptive media portion of the device.

Another aspect of the present invention relates to methods for separating or purifying a desired product or biological molecules of interest from a sample or mixture which comprises preequilibrating a device of the present invention with a buffer solution, loading the resulting preequilibrated device with a sample or mixture which comprises the desired product or biological molecules of interest and undesired impurities, then washing the loaded device with a buffer (1), and thereafter charging the device with a preferred buffer (2) which saturates the size exclusion media in the device of the present invention, eluting the biological molecules of interest by loading the device with a volume an elution buffer (3) and collecting the biological molecules of interest in the preferred buffer (2).

In a preferred embodiment, the volume of elution buffer (3) present is about 5% to about 50% of the volume of size exclusion media packed into the device of the present invention.

In another embodiment, preferred buffer (2) is present in a volume which comprises the total volume of adsorptive media and size exclusion media packed in the device of the present invention, and optionally, an additional volume which is in the range of about 1% to about 600% of the total volume of adsorptive media and size exclusion media packed into the device. In a preferred embodiment, the additional volume of preferred buffer (2) is about 5% to about 400%, and more preferably, about 10% to about 60% of the total volume of adsorptive media and size exclusion media packed into the device of the present invention.

A further aspect the present invention relates to a device for purifying a desired product or biological molecules of interest which comprises a housing having an outlet disposed at a bottom end, wherein a porous material is disposed over the outlet, a size exclusion media portion comprising a volume of a size exclusion media packed in the housing on top of said porous material, and a surfactant portion comprising a surfactant layer disposed on top of said size exclusion media portion.

DETAILED DESCRIPTION OF THE INVENTION

The present invention relates to a device for separation or purification of a solute of interest using a device wherein a volume of adsorptive media is loaded on top of a volume of SEC media. The solute of interest is adsorbed onto the adsorptive media, but is excluded from the SEC media upon elution.

In the present specification, the terms "size exclusion chromatography media", "SEC media", and "size exclusion media" will be used interchangeably to refer to the size exclusion chromatography media used in the present invention.

Figure 1:
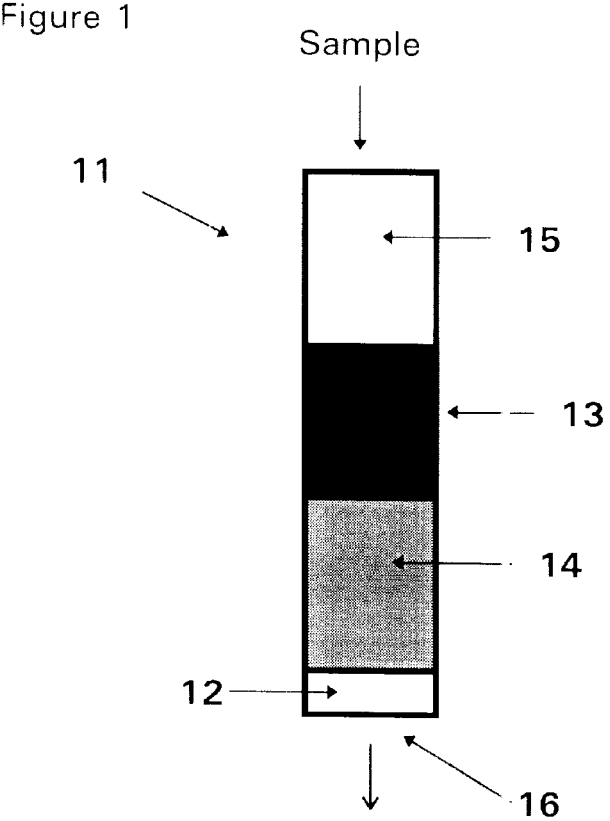
FIG. 1 depicts a side view of a device according to the present invention wherein a housing (11) having an opening (16) in the bottom of the housing and a porous material (12) disposed over the opening, is loaded with adsorptive media (13), which is loaded on top of an SEC media (14), leaving a reservoir (15) above the adsorptive media (13).

According to the present invention, in order to purify or separate biological molecules, the SEC step is combined with the adsorptive step in a single device, as shown in FIG. 1. The device of the present invention is particularly useful for purifying or separating products that are much larger than the undesired molecules contained in the elution buffer, such that, on a relative basis, the desired product is excluded from the SEC media, while the undesired molecules in the buffer enter the SEC media.

The present invention allows the desired product to be eluted in any buffer of choice in a single or "one step" process in a small laboratory device or high speed device. The buffer of choice can be any relatively small molecular weight compound compared with the molecular weight of the desired product. Examples of such buffers include low molecular weight TRANSFECTAM™, low molecular weight polyethyleneimine ("PEI"), and Tris HCl of any salt concentration or desired pH.

Using the device of the present invention, the desired product or solute of interest is adsorbed onto the adsorptive media. It is then washed with a buffer (1) in order to remove loosely bound solutes. Then, the device is loaded with a preferred buffer (2) to charge the SEC media portion of the device with the preferred buffer (2).

An elution buffer (3) is then passed through the device or column, which causes the desired product to desorb from the adsorptive media. The solute then passes into the SEC media section of the device, and a typical size exclusion (e.g., desalting) operation occurs. The desired product or solute of interest is excluded from the interior part of the SEC media. Thus, the desired product or solute of interest travels faster in the SEC media portion of the device than does the elution buffer (3). The desired product or solute of interest therefore overtakes the preferred buffer (2) and exits the device in this preferred buffer (2). The volume of the elution buffer (3) is carefully controlled so that it remains in the device, and does not exit with the desired product and the preferred buffer (2).

The geometry of the device of the present invention, and the reservoir for the buffers can be varied for convenience.

Adsorptive chromatography media for use in the device of the present invention include, but are not limited to, media such as reversed phase media, ion exchange media, normal phase media, hydroxyapitite media, metal chelating media, affinity media, and any other media which binds molecules in one buffer, and releases molecules in a different buffer. For example, adsorptive chromatography media may be selected from the group consisting of PLASMIDEX™ 20μ (commercially available from BioSepra, Inc., Marlborough, Mass. USA),), Q FAST FLOW™ (commercially available from Pharmacia Biotech, Uppsala Sweden), QIAGEN PLASMID MEDIA™ (commercially available from Qiagen Inc., Chatsworth, Calif. USA).

The amount of adsorptive media present in the device of the present invention can vary depending on the adsorptive media used and the size of the device housing. In general, the packed volume of media used as the adsorptive media portion of the device of the present invention is about 10 μl to about 2000 μl. Preferably, the packed volume of the adsorptive media portion is about 10 μl to about 50 μl, and more preferably about 15 μl to about 25 μl.

Media useful as size exclusion or SEC media in the device of the present invention should allow the impurities in a sample to penetrate the SEC media to a greater extent than the desired product or solute of interest in the sample. In addition, the SEC media should be rigid enough to allow a useful pressure drop in order to force flow through the media. For example, SEC media for use in the present invention include, but are not limited to, ACA™ media, such as ACA 34™, ACA 44™, ACA 54™, and ACA 200™ (commercially available from BioSepra, Inc., Marlborough, Mass. USA), GF05™ and GF2000™ (commercially available from BioSepra, Inc., Marlborough, Mass. USA), Sephacryl™ media, such as S400™, S500™, and S-1000™ (commercially available from Pharmacia Biotech, Uppsala, Sweden), Superdex™ media, such as Superdex 75™ and Superdex 200™ (commercially available from Pharmacia Biotech, Uppsala, Sweden), and the like. In one embodiment, the size exclusion media is a SEC desalting media.

The present invention can further be used to remove any lower molecular weight compounds, including but not limited to, proteins, enzymes, endotoxins, and RNA, from a sample, such as a plasmid-containing sample, by selection of an appropriate SEC media. The characteristics of various SEC media which may be used in the present invention are known in the art, and thus selection of an appropriate SEC media for purification of a particular sample will be readily apparent to the skilled artisan.

The amount of SEC media present in the device of the present invention can vary depending on the SEC media used and the size of the device housing. In general, the packed volume of media used in the size exclusion media portion of the device of the present invention is about 30 μl to about 6000 μl. Preferably, the packed volume of size exclusion media is about 40 μl to about 300 μl, and more preferably about 45 μl to about 100 μl.

In general, when used in the methods for separating or purifying a desired product or solute of interest according to the present invention, the packed volume of the SEC media should be between about 2 times to about 10 times the volume of the elution buffer (3).

In other embodiments, the SEC media portion of the device of the present invention can be changed to various other media having different adsorptive characteristics from the main adsorptive media, including but not limited to, hydrophobic interaction media which may selectively retain (or repel) the desired product, but repel (or retain) the buffer. An example of hydrophobic interaction media is media which will bind proteins at high salt concentrations, but elute proteins at low salt concentrations, thus effecting a one step separation of the desired product from other solutes in the first adsorptive media portion of the device, and then the desired product from the undesired elution buffer (salt) in the hydrophobic interaction media portion of the device.

Housings for use in the present invention can be readily determined by the skilled artisan. Such housings may include, but are not limited to, syringe-like devices, tubes, and wells of a multiwell plate, including, but not limited to 4-well, 16-well, 96-well, and 364-well multiwell plates. A porous material, such as a porous frit or membrane, is placed in the bottom of the housing prior to loading the various media in order to prevent the media from seeping out of the bottom hole of the housing during loading. Porous materials, including but not limited to porous frits or membranes, which may be used in the device of the present invention are well known in the art. Examples of porous frits include, but are not limited to, polypropylene frits having pore sizes ranging from about 0.45 μm to about 50 μm, and preferably from about 1 μm to about 20 μm (such frits are commercially available from Porex Technologies, Fairburn, Ga. USA).

In one embodiment of the device of the present invention, the device may further include a removable porous material, such as a porous frit or membrane, disposed on top of the adsorptive media portion of the device. This removable porous material may be left in place or removed when using the device to perform purification or separation operations, and preferably, the removable porous material is removed prior to use.

The present invention also relates to a method for purifying a desired product or biological molecule of interest using the device of the present invention. Essentially, the device of the present invention is preequilibrated with a buffer solution, then the resulting preequilibrated device is loaded with a sample or mixture comprising the desired product and undesired impurities. Thereafter, the loaded device is washed with a buffer (1), wherein said buffer (1) removes loosely bound impurities from the device while leaving the desired product in the device. The device is then washed with a preferred buffer (2), wherein preferred buffer (2) flows through an adsorptive media portion of the device into a size exclusion media portion of the device, and the volume of preferred buffer (2) is sufficient to saturate the size exclusion media with the preferred buffer (2). The desired product is then eluted using a predetermined volume of an elution buffer (3), wherein the volume of elution buffer (3) is controlled to avoid elution with the desired product and preferred buffer (2).

The present invention provides the advantage of a combined or "one step" adsorptive and size exclusion (e.g., desalting) process, for delivering a desired solute of a relatively high molecular weight in a buffer of relatively low molecular weight which does not interfere with subsequent use of the desired solute, while removing the desired solute from the elution buffer. Thus, the device and methods of the present invention minimize the number of steps and amount of equipment required, and saves the user time and money.

Preequilibration buffers for use in the present invention may include, but are not limited to, 50 mM Tris pH 8, 0 to 2 M NaCl or 50 mM MOPS 0–2 M NaCl, or other buffer/salt combinations. In general, the pH of the preequilibration buffer will be in the range of about pH 1 to about pH 12. A preferred preequilibration buffer is 500 mM NaCl, 50 mM Tris pH 8.

Buffers for use as buffer (1), or the wash buffer according to method of the present invention generally are selected from salt buffers, wherein the choice of salt is dictated by what salt could elute the impurities but not the desired product, e.g., plasmids, in a particular sample. Examples of buffers suitable for use as buffer (1) include, but are not limited to, 500 mM to 2 M NaCl in a buffer such as Tris pH 8, Tris pH 7, MOPS, or other suitable buffers.

Buffers for use as the preferred buffer (2) according to the methods of the present invention are selected from buffers or buffer combinations which are compatible with further processing of the desired product, such as a plasmid. Examples of buffers suitable for use as preferred buffer (2) include, but are not limited to, water, 50 mM Tris, 50 mM Tris and 5 mM EDTA, TRANSFECTUM™, SUPERFECTUM™, LIPOFECTUM™, enzymatic digest solutions containing enzymes or endonucleases, such as HindIII, EcoRI or other enzymes useful for sequencing of DNA, and the like, and combinations thereof.

The volume of preferred buffer (2) used in the methods of the present invention should be sufficient to saturate the SEC media portion of the device. In general, the volume of preferred buffer (2) used will be roughly equal to the packed volume of the adsorptive media in the device plus the packed volume of the SEC media in the device, and may optionally include an additional volume for robustness, which additional volume is in the range of about 1% to about 600% of the total packed volume of the media loaded into the device, and preferably about 5% to about 400%, and more preferably, about 10% to about 60% of the total packed volume of media loaded into the device.

Buffers for use as elution buffer (3), or the elution buffer, according to methods of the present invention include high salt buffers, such as NaCl, KCl, $MgCl_2$, or $CaCl_2$ buffered with buffers known to those skilled in the art, such as Tris buffer, MOPS buffer, Acetate buffer, phosphate buffer, and the like.

The volume of the elution buffer (3) should be carefully controlled such that the elution buffer does not leave the device, or that the elution buffer leaves the device at a specific and predictable volume, so that the elution buffer does not mix with the desired product which is in preferred buffer (2). In general, the volume of elution buffer (3) used in the method of the present invention will be in the range of about 5% to about 50% of the packed volume of the SEC media.

When using the methods of the present invention to purify a desired product or solute of interest, it is preferable that the buffers used for both preferred buffer (2) and elution buffer (3) do not have a molecular weight on the same order as the molecular weight of the desired product or solute of interest.

Various types of samples may be purified using the present invention, including, but not limited to, a crude plasmid solution, such as that obtained from potassium acetate precipitation according to known methods (see, e.g., *Molecular Cloning*, Sambrook, Fritsch, Maniatas, Cold Spring Harbor, Plainview, N.Y. (1989)), and plasmid or genomic DNA prepared using a variety of other methods well known in the art. In one embodiment, the sample containing the desired product is a clear *E. coli* cell lysate which is precipitated with potassium acetate, such as 1.32 M potassium acetate at pH 4.8.

In general, the desired product or solute of interest to be purified from a sample according to the present invention should be sufficiently larger than the undesirable molecules and impurities contained in the sample, such that on a relative basis, during the elution step of the present invention, the desired product or solute of interest would be excluded from the SEC media while the undesirable molecules and impurities would enter the SEC media. In this manner, any smaller molecular weight molecules, such as RNA, endotoxins, proteins, etc., can be separated from larger molecular weight molecules, such as plasmid DNA and genomic DNA, by using an appropriately sized SEC media, wherein said SEC media is sized with respect to the exclusion limit of the SEC media.

Note that while endotoxins are smaller molecular weight molecules than plasmids and other large nucleic acids, it is known that endotoxins can typically be found in micelles, which have a very large effective size, and do not enter the pores of most SEC media. Also, endotoxin micelles often coelute from ion exchangers with plasmids and other large nucleic acids. These endotoxins are not, however, desirable in plasmid preparations. Thus, it is desirable to separate endotoxins from the desired plasmid or other larger molecular weight products.

Accordingly, surfactants may be used to break up endotoxin micelles, thereby making the endotoxins small enough to enter the pores of a SEC media and be retained by the media relative to the desired product, such as plasmids or larger molecular weight molecules. Thus, the elution buffer (3) for removing the desired product from, for instance, the adsorptive media may comprise a high salt buffer in order to elute the desired product and an amount of a surfactant such that endotoxin micelles are broken up. The elution buffer (3) then pushes both the desired product and endotoxins into the SEC media portion of the device, where the endotoxins are retained by the SEC media, and the desired product goes through the interstices of the SEC media and elutes in preferred buffer (2). Surfactants, e.g., such as 1% to 10% Triton X100™ or X114™, or sodium dodecyl sulfate ("SDS"), are small molecular weight solutes, and are retained by the SEC media. Hence, the SEC media retains the salt, surfactant, endotoxins, and other small molecule impurities, including RNA and proteins, while the desired product is eluted in preferred buffer (2).

Accordingly, in another embodiment of the present invention, elution buffer (3) comprises a salt buffer to desorb the desired product, such as plasmids or other large molecular weight molecules, from the adsorptive media portion of the device of the present invention and a surfactant to break up endotoxin micelles. Surfactants for use in elution buffer (3) include, but are not limited to, Triton X100™, Triton X114™, SDS, Brij™, and other similar surfactants. Triton X™ (Union Carbide Corporation, Danbury, Conn. USA) is a series of octylphenoxypolyethoxyethanols having between 1 and 70 oxyethylene repeating units; Brij™ (ICI Surfactants, Wilmington, Del. USA) is a series of polyoxyethylene ethers of $C_{12}$ to $C_{18}$ alcohols.

Figure 2:
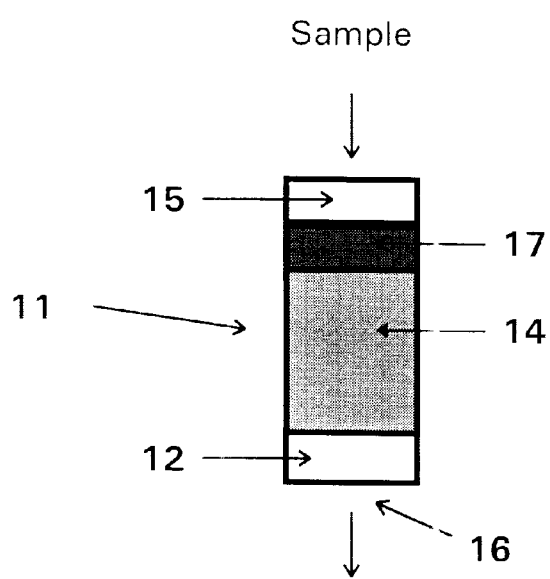
FIG. 2 depicts a side view of another device according to the present invention wherein a housing (11) having an opening (16) in the bottom of the housing and a porous material (12) disposed over the opening, is loaded with a thin layer of a surfactant (17) which is loaded on top of an SEC media (14), leaving a reservoir (15) above the surfactant (17).

In another embodiment, the present invention relates to a device for purifying a desired product or solute of interest, such as plasmid DNA or genomic DNA, which comprises a housing having a porous material, such as a porous frit or membrane, on the bottom thereof, loaded with a thin layer of surfactant which is loaded on top of a SEC media, as shown in FIG. 2. This device may be used to separate a desired product, such as a plasmid or other large molecular weight molecule, by precharging the SEC media with preferred buffer (2), loading the device with a sample or mixture containing the desired product and undesired impurities, and eluting the desired product using any appropriate buffer. According to this method, the surfactant layer of the device contacts the sample comprising the desired product and impurities, such as endotoxins, upon their delivery to the device, and any endotoxin micelles present in the sample disintegrate. Subsequently, the disintegrated endotoxin micelles enter the pores of the SEC media, while the desired product passes through the surfactant and elutes through void volume of the SEC media in preferred buffer (2) which is precharged in the SEC media.

The invention is further defined by reference to the following examples that describe in detail preparation of a one step device for purifying a desired product or biological molecule of interest, and methods of using the same according to the present invention. It will be apparent to those skilled in the art that many modifications, both to materials and methods, may be practiced without departing from the purpose and scope of this invention. The following examples are illustrative only and should in no way limit the scope of the present invention.

EXAMPLE 1

Clear lysate samples were prepared in the following manner for use the examples herein. E. coli DH5α containing the plasmid pSV-βGAL was inoculated into each of several flasks containing 120 ml of LB/Amp β-galactose media, and grown overnight at 37° C. The cultures were then harvested by centrifuging in a Beckman G6 centrifuge for 15 minutes at about 3000 rpm.

The resulting pellets were then each resuspended in 5 ml of resuspension media (Promega, Madison, Wis. USA), and RNAase (Qiagen Inc., Chatsworth, Calif. USA) was added to a concentration of 100 $\mu$g/ml. 5 ml of lysis buffer (Promega, Madison, Wis. USA) was then added, the samples were inverted, and allowed to sit for 5 minutes at room temperature.

Thereafter, 5 ml of neutralization buffer (Promega, Madison, Wis. USA) was added to each sample, the samples mixed and inverted, and spun in a Sorval, SS 34 rotor for 30 minutes at about 12,000 rpm.

The resulting supernatants were then collected in 3 ml aliquots, and frozen for later use.

Prior to using the lysate samples in the subsequent examples, the frozen lysate samples were thawed, and precleared by spinning for about 8 minutes at 4° C., and then the cleared lysates were transferred to new tubes.

EXAMPLE 2

In 3 mm diameter tubes having frits fitted into the bottom, the following media were loaded:

TABLE 1

|  | Desalting Media | Adsorption Media |
|---|---|---|
| Tube 1 | 150 $\mu$l of 50% ACA 44 ™ Slurry | 50 $\mu$l of 40% PLASMIDEX ™ 20$\mu$Slurry |
| Tube 2 | — | 50 $\mu$l of 40% PLASMIDEX ™ 20$\mu$ Slurry |
| Tube 3 | — | 37.5 $\mu$l of 40% PLASMIDEX ™ 20$\mu$ slurry |
| Tube 4 | — | 37.5 $\mu$l of 40% PLASMIDEX ™ 20$\mu$ slurry |

Tube 1 was first packed with 150 $\mu$l of a 50% ACA 44™ slurry (commercially available from BioSepra, Inc., Marlborough, Mass. USA), and vacuumed from the bottom of the tube to remove excess fluid from the top of the bed. Tube 1 was then packed with 50 $\mu$l of a 40% PLASMIDEX™ 20$\mu$ slurry (a 20 $\mu$m quaternary amine anion exchange media commercially available from BioSepra, Inc., Marlborough, Mass. USA), and vacuumed again from the bottom to remove excess interstitial fluid. Similarly, Tube 2 was packed with 50 $\mu$l of 40% PLASMIDEX™ 20$\mu$ slurry, and Tubes 3 and 4 were each packed with 37.5 $\mu$l of 40% PLASMIDEX™ 20$\mu$ slurry.

Each of Tubes 1 through 4 were then preequilibrated with 400 $\mu$l of 0.5 M NaCl, 50 mM Tris pH 7.0.

600 $\mu$l of a sample from Example 1, which comprise a clear lysate from a culture of E. coli DH5α containing pSV-βGAL (the desired plasmid product) and undesirable contaminants, was then added to each of Tubes 1, 2, 3 and 4. The flow through from each tube was collected, and designated as samples 1f, 2f, 3f, and 4f, respectively.

Each tube was then washed with 400 $\mu$l of 0.5 M NaCl, 50 mM Tris pH 7.0. The wash from Tubes 1, 2, 3, and 4 were collected and labeled as samples 1w, 2w, 3w, and 4w, respectively. In addition, Tube 1 was loaded with 400 $\mu$l of distilled water (as preferred buffer (2)).

Each tube was then eluted twice with 25 $\mu$l of the following elution buffers:

| | |
|---|---|
| Tubes 1 and 2 | 2M NaCl, 50 mM Tris pH 8.5; |
| Tube 3 | 2M CaCl$_2$, 50 mM Tris pH 8.5; and |
| Tube 4 | 2M NaCl, 50 mM Tris pH 8.5. |

Flow through was collected after each elution step, and the samples for Tubes 1, 2, 3, and 4 from the first elution step were designated 1e$_1$, 2e$_1$, 3e$_1$, and 4e$_1$, respectively, and the samples from the second elution step were designated 1e$_2$, 2e$_2$, 3e$_2$, and 4e$_2$, respectively.

Except for elution samples 1e$_1$ and 1e$_2$ collected from Tube 1, in order to aid in precipitation, to each of the elution samples the following were added: 12.5 μl of 2 M NaCl, 165 μl of TE Buffer, and 140 μl isopropanol. 420 μl of isopropanol were added to each of the flow through samples 1f, 2f, 3f, and 4f, and 280 μl of isopropanol were added to each of the wash samples 1w, 2w, 3w, and 4w. These samples were then vortexed and allowed to sit on ice for 60 minutes.

The samples were then centrifuged in a Beckman G6 centrifuge for 20 minutes, and the supernatant decanted. Each tube was then washed with 500 μl of 70% ethanol at −20° C., centrifuged for 6 minutes, and the supernatant decanted. The tubes were then allowed to air dry for 30 minutes, and were resuspended in 30 μl of TE Buffer.

5 μl of each sample, including samples 1e$_1$ and 2e$_2$, were then loaded onto a 1% agarose gel run at 100 V for 60 minutes. More specifically, lanes 1 through 4 were loaded with 5 μl of samples 1f, 1w, 1e$_1$, and 1e$_2$, respectively; lanes 5 through 8 were loaded wit 5 μl of samples 2f, 2w, 2e$_1$, and 2e$_2$, respectively; lanes 9 through 12 were loaded with 5 μl of samples 3f, 3w, 3e$_1$, and 3e$_2$, respectively; and lanes 13 through 16 were loaded with 5 μl of samples 4f, 4w, 4e$_1$, and 4e$_2$, respectively.

In addition, a 1/50 dilution of each elution sample and a 1/25 dilution of each flow through and wash sample were placed in quartz cuvettes, and the optical density ("OD") of each sample was measured using a UV spectrometer at 260 nm and 280 nm. The results from the UV spectroscopy are set forth in Table 2.

TABLE 2

| Sample | Sample Volume | 260 nm | 280 nm | ratio 260:280 | mg/ml | Yield (g) |
|---|---|---|---|---|---|---|
| 1f | 30 μl | 0.006 | 0.005 | 1.2 | 0.008 | 0.2 μg |
| 1w | 30 μl | 0.005 | 0.004 | 1.2 | 0.006 | 0.2 μg |
| 1e$_1$ | 25 μl | 0.402 | 0.202 | 1.99 | 1.005 | 25.1 μg |
| 1e$_2$ | 25 μl | 0.085 | 0.044 | 1.93 | 0.213 | 5.3 μg |
| 2f | 30 μl | 0.006 | 0.004 | 1.2 | 0.008 | 0.2 μg |
| 2w | 30 μl | 0.004 | 0.003 | 1.3 | 0.005 | 0.2 μg |
| 2e$_1$ | 30 μl | 0.411 | 0.216 | 1.9 | 1.028 | 30.9 μg |
| 2e$_2$ | 30 μl | 0.014 | 0.008 | 1.75 | 0.035 | 1.1 μg |
| 3f | 30 μl | 0.010 | 0.006 | 1.67 | 0.013 | 0.4 μg |
| 3w | 30 μl | 0.005 | 0.004 | 1.3 | 0.006 | 0.2 μg |
| 3e$_1$ | 30 μl | 0.365 | 0.187 | 1.95 | 0.913 | 27.4 μg |
| 3e$_2$ | 30 μl | 0.049 | 0.026 | 1.88 | 0.123 | 3.7 μg |
| 4f | 30 μl | 0.043 | 0.025 | 1.72 | 0.054 | 1.6 μg |
| 4w | 30 μl | 0.005 | 0.004 | 1.3 | 0.006 | 0.2 μg |
| 4e$_1$ | 30 μl | 0.228 | 0.118 | 1.93 | 0.570 | 17.1 μg** |
| 4e$_2$ | 30 μl | 0.012 | 0.008 | 1.5 | 0.030 | 0.9 μg |

*The mass indicated is for the original sample based on the elution volume and the A260 reading, which reads 1 AU for 50 g/ml.
**The yield of de$_1$ is underrepresented, due to less RNA contaminants in the preparation as indicated in the gel.

The results set forth in Table 2 above, those obtained with the agarose gel run, indicate that excellent recovery was obtained using Tube 1 containing the ACA 44™ media, and the gel electrophoresis results indicate that the ACA 44™ media in Tube 1 properly desalted the desired plasmid product.

EXAMPLE 3

Each of two wells of a 96-well filter plate (Polyfiltronics, Rockland, Mass. USA), were loaded with 150 μl of 40% PLASMIDEX™ 20μ slurry, and designated Wells 1 and 2. A third well of the 96-well filter plate was loaded with 500 μl of 50% ACA 34™ slurry, and designated Well 3. The plate was then spun for 1 minute using a Beckman G6 centrifuge at 2000 rpm (360 g) to remove excess fluid. Thereafter, in Well 3, 150,μl of 40% PLASMIDEX™ 20μ slurry was added on top of the ACA 34, and the plate was spun again for 1 minute.

Each of Wells 1 to 3 were then preequilibrated with 600 μl of 0.5 M NaCl, 50 mM Tris pH 7.0. Thereafter, 600 μl of a sample from Example 1, which comprise a clear lysate from a culture of E. coli DH5α containing pSV-βGAL (the desired plasmid product) and undesirable contaminants, was added to each of Wells 1, 2, and 3. The plate was then spun for 5 minutes in the centrifuge. The flow through from each well was collected, and designated as samples 1f, 2f, and 3f, respectively.

Each well was then washed with 600 μl of 0.5 M NaCl, 50 mM Tris pH 7.0, and the plate was then spun for 3 minutes in the centrifuge. The wash from Wells 1, 2, and 3 were collected and labeled as samples 1w, 2w, and 3w, respectively. Thereafter, Well 3 was loaded with 600 μl distilled water (as preferred buffer (2)).

Each well was then eluted with 100 μl of 2 M NaCl, 50 mM Tris pH 8.5; and soaked for 2 minutes. Thereafter, the plate was spun in the centrifuge for 2 minutes and the elution samples were collected and designated as samples 1e, 2e, and 3e, respectively.

Standard isopropanol precipitation was then performed on each of the crude lysate samples, flow through samples, wash samples, and elution samples 1e and 2e, wherein a volume of isopropanol equal to about 70% of the volume of the sample is added to each sample, vortexed, and allowed to sit on ice for about 60 minutes. These samples were then centrifuged in a Beckman G6 centrifuge for about 10 minutes at about 14,000 rpm, and the supernatant decanted. Each tube was then washed with 600 μl of 70% ethanol at −20° C., centrifuged for 6 minutes, and the supernatant decanted. The tubes were then allowed to air dry for 20 minutes, and were resuspended in 100 μl of TE Buffer.

5 μl of each sample collected, as well as 5 μl of the crude lysate samples used, were then loaded onto a 1% agarose gel run at 100 V for 60 minutes. The lanes of the gel contained the following samples: lane 1 was loaded with 5 μl of isopropanol precipitated crude lysate sample used in Wells 2 and 3; lane 2 was loaded with 5 μl of isopropanol precipitated crude lysate sample used in Well 1; lanes 4 through 6 were loaded with 5 μl of samples 1f, 1w, and 1e, respectively; lanes 8 through 10 were loaded with 5 μl of samples 2f, 2w, and 2e, respectively; and lanes 12 through 14 were loaded with 5 μl of samples 3f, 3w, and 3e, respectively.

Results from the agarose gel run, especially for the elution sample 3e (lane 14), indicate that good desalting of the plasmid sample was obtained using the ACA 34™ media situated in the well beneath the PLASMIDEX™ 20μ media.

EXAMPLE 4

Each of two, 3 mm diameter tubes having a porous frit in the bottom were loaded with 150 μl of a 75% GF05™ media slurry, and a third tube was loaded with 100 μl of the 75% GF05™ media slurry. The tubes were then vacuumed from the bottom to remove excess fluid, and designated as Tubes 1, 2, and 3, respectively. Each of Tubes 1, 2, and 3 were then loaded with 37.5 μl of a 40% PLASMIDEX™ 20μ slurry (BioSepra Inc., Marlborough, Mass. USA), and vacuumed from the bottom to remove excess liquid.

In addition, a well of a 96-well filter plate (Polyfiltronics, Rockland, Mass. USA) was loaded with 400 μl of a 75% GF05 media slurry, and then to remove excess fluid, the plate was spun in a Beckman G6 centrifuge for about 2 minutes at 1800 rpm. The well was then loaded with 375 μl of a 40% PLASMIDEX™ 20μ slurry, and spun in the centrifuge for about 3 minutes at 1800 rpm. A porous polypropylene frit having pores of about 7 μm, was placed on top of the packed PLASMIDEX™ 20μ media, and this well is designated Tube 4.

The tubes were then all preequilibrated with 400 μl of 0.5 M NaCl, 50 mM Tris pH 7.0. Thereafter, 400 μl of samples comprising clear E. coli lysates according to Example 1 containing the desired pSV-βGAL plasmid product and undesirable contaminants, were then added to each of Tubes 1 to 3, and 600 μl of a clear E. coli lysate sample was added to Tube 4. The tubes were vacuumed and the flow through from each tube was collected, and designated as samples 1f, 2f, 3f, and 4f, respectively.

Each tube was then washed with 400 μl of 0.5 M NaCl, 50 mM Tris pH 7.0, and the wash from Tubes 1 to 4 was collected and labeled as samples 1w, 2w, 3w, and 4w, respectively. Thereafter, each tube was loaded with 400 μl of 50 mM Tris pH 7.0 (as preferred buffer (2)).

Tubes 1 and 2 were then eluted twice with 25 μl of 1.5 M NaCl, 50 mM Tris pH 8.5 with 2.5 μg/ml RNAse. After each elution step, the tubes were vacuumed and elution samples were collected, and were designated $1e_1$, $1e_2$, $2e_1$, and $2e_2$, respectively. Tube 3 was eluted twice with 25 μl of 2 M NaCl, 50 mM Tris pH 8.5, and samples were collected after each elution step as above, and designated $3e_1$ and $3e_2$. Tube 4 was eluted first with 100 μl of 1 M NaCl, 50 mM Tris pH 8.5, which was allowed to soak for 2 minutes, and then the plate was spun on the centrifuge for 5 minutes, and an elution sample designated $4e_1$ was collected. Tube 4 was then eluted a second time with 100 μl of 2 M NaCl, 50 mM Tris pH 8.5, which was allowed to soak for 2 minutes, and then the plate was spun on the centrifuge for 5 minutes, and an elution sample designated $4e_1$ was collected.

An EcoRI (10××) restriction enzyme digest solution was made by combining 60 μl of distilled water, 10 μl of 10× buffer H, and 5 μl of EcoRI. Similarly, an HindIII (10××) restriction enzyme digest solution was made by combining 60 μl of distilled water, 10 μl of 10× buffer H, and 5 μl of HindIII.

EcoRI digestion samples were then made for i) samples $1e_1$, $2e_1$, $2e_2$, $3e_1$, $4e_1$, and $4e_2$ of this example, ii) sample $4e_1$ from Example 2, and iii) crude E. coli DH5α lysate sample by mixing in a tube 7.5 μl of EcoRI restriction enzyme digest solution with 2.5 μl of the sample, allowing to stand at 37° C. for 2 hours, and then adding 2.5 μl of 6× loading buffer.

Similarly, HindIII digestion samples were made for i) samples $1e_1$, $2e_1$, $2e_2$, $3e_2$, $4e_1$, and $4e_2$ of this example, ii) sample $4e_1$ from Example 2, and iii) crude E. coli DH5α lysate sample by mixing in a tube 7.5 μl of HindIII restriction enzyme digest solution with 2.5 μl of the sample, allowing to stand at 37° C. for 2 hours, and then adding 2.5 μl of 6× loading buffer.

5 μl of each sample were then loaded onto a 1% agarose gel in the lanes indicated Table 3 below, and the gel was run at 100 V for 60 minutes.

TABLE 3

| LANE NO. | SAMPLE | RESTRICTION ENZYME |
|---|---|---|
| 1 | λ HindIII marker | HindIII |
| 2 | crude E. coli DR5α lysate sample used in Example 4 | none |
| 3 | $1e_2$ from Example 4 | none |
| 4 | $3e_2$ from Example 4 | none |
| 5 | $1e_1$ of Example 4 | EcoRI |
| 6 | $1e_1$ of Example 4 | HindIII |
| 7 | $2e_1$ of Example 4 | EcoRI |
| 8 | $2e_1$ of Example 4 | HindIII |
| 9 | $2e_2$ of Example 4 | EcoRI |
| 10 | $2e_2$ of Example 4 | HindIII |
| 11 | $3e_1$ of Example 4 | EcoRI |
| 12 | $3e_2$ of Example 4 | HindIII |
| 13 | crude E. coli DH5α lysate | EcoRI |
| 14 | crude E. coli DH5α lysate | HindIII |
| 15 | $4e_1$ of Example 2 | EcoRI |
| 16 | $4e_1$ of Example 2 | HindIII |
| 17 | $4e_1$ from Example 4. | EcoRI |
| 18 | $4e_1$ from Example 4 | HindIII |
| 19 | $4e_2$ from Example 4 | EcoRI |
| 20 | $4e_2$ from Example 4 | HindIII |

The results obtained with the gel indicate that the present invention provides good separation of the desired plasmid product from the sample, and the resulting purified plasmid product may be satisfactorily used in subsequent processing steps The embodiments of the present invention described above are intended to be merely exemplary and those skilled in the art will recognize, or be able to ascertain using no more than routine experimentation, numerous equivalents to the specific procedures described herein. All such equivalents are considered to be within the scope of the present invention and are covered by the following claims.

The contents of all references described herein are hereby incorporated by reference. Other embodiments are within the following claims.

What is claimed is:

1. A device for purification of biological molecules comprising:
   a housing, wherein said housing has an outlet at a bottom end and a porous material disposed at the bottom end;
   a size exclusion media portion comprising a volume of a size exclusion media packed in the housing on top of said porous material; and
   an adsorptive media portion comprising a volume of adsorptive media packed in the housing on top of said size exclusion media portion.

2. The device of claim 1, further comprising a reservoir, wherein said reservoir is disposed above the adsorptive media portion of the device.

3. The device of claim 1, further comprising a second removable porous material, wherein said second removable porous material is disposed on top of said adsorptive media portion of the device.

4. The device of claim 1, wherein the housing comprises a well of a multiwell plate.

5. The device of claim 1, wherein said porous material is a porous polypropylene frit.

6. The device of claim 4, wherein the adsorptive media is selected from the group consisting of ion exchange media, affinity media, normal phase media, reverse phase media, metal chelating media, and hydroxyapitite media.

7. The device of claim 1, wherein a packed volume of the adsorptive media packed in the device is in the range of about 10 μl to about 2000 μl.

8. The device of claim 7, wherein the packed volume of the adsorptive media in the device is in the range of about 10 µl to about 50 µl.

9. The device of claim 8, wherein the packed volume of the adsorptive media in the device is in the range of about 15 µl to about 25 µl.

10. The device of claim 1, wherein said size exclusion media is a size exclusion chromatography desalting media.

11. The device of claim 1, wherein a packed volume of the size exclusion media in the device is in the range of about 30 µl to about 6000 µl.

12. The device of claim 11, wherein the packed volume of the size exclusion media in the device is in the range of about 40 µl to about 300 µl.

13. The device of claim 12, wherein the packed volume of the size exclusion media in the device is in the range of about 45 µl to about 100 µl.

14. A method for separating biological molecules of interest from a sample comprising the steps of:
(a) preequilibrating the device of claim 1 with a buffer solution;
(b) loading the resulting preequilibrated device with a sample comprising a mixture of the biological molecules of interest and undesired impurities;
(c) washing the loaded device with a buffer (1);
(d) charging the device with a preferred buffer (2), wherein said preferred buffer (2) saturates the size exclusion media portion of the device;
(e) eluting the biological molecules of interest with a volume an elution buffer (3); and
(f) collecting the resulting elutant, wherein said elutant comprises the biological molecules of interest in the preferred buffer (2).

15. The method of claim 14, wherein said buffer (1) removes loosely bound impurities while leaving the desired biological molecules of interest adsorbed to the adsorptive media portion of the device.

16. The method of claim 14, wherein the volume of elution buffer (3) present is in the range of about 5% to about 50% of the volume of size exclusion media packed into the device.

17. The method of claim 14, wherein the preferred buffer (2) is present in a volume about equal to the total volume of media in the device, wherein said total volume is the volume of size exclusion media plus the volume of adsorption media present in the device.

18. The method of claim 14, wherein the volume of preferred buffer (2) is in the range of about 1% to about 600% greater than the total volume of media in the device, said total volume of media in the device being the volume of size exclusion media plus the volume of adsorption media present in the device.

19. The method of claim 18, wherein the volume of preferred buffer (2) is in the range of about 5% to about 400% greater than the total volume of media in the device.

20. The method of claim 19, wherein the volume of preferred buffer (2) is in the range of about 10% to about 60% greater than the total volume of media in the device.

21. The method of claim 14, wherein the biological molecules of interest are selected from the group consisting of plasmid DNA and genomic DNA.

22. A device for purification of biological molecules comprising:
a housing, wherein said housing has an outlet at a bottom end and a porous material disposed at the bottom end;
a size exclusion media portion comprising a volume of a size exclusion media packed in the housing on top of said porous material; and
a surfactant portion comprising a surfactant layer disposed on top of said size exclusion media portion.

23. The device of claim 22, wherein said surfactant layer comprises a surfactant selected from the group consisting of sodium dodecyl sulfate, polyoxyethylene (10) isooctylphenyl ether, polyoxyethylene (8) isooctylphenyl ether and polyoxyethylene ethers of $C_{12}$ to $C_{18}$ alcohols.

24. A method for purifying a biological molecule of interest, comprising the steps of:
(a) precharging the device of claim 22 with a preferred buffer (2), wherein said preferred buffer (2) saturates the size exclusion media portion of the device;
(b) loading the resulting precharged device with a sample comprising a mixture of the biological molecules of interest and undesired impurities;
(c) eluting the biological molecules of interest with a volume of an elution buffer (3); and
(d) collecting the resulting elutant, wherein said elutant comprises the biological molecules of interest.

* * * * *